United States Patent
Fiey et al.

(10) Patent No.: US 9,534,078 B2
(45) Date of Patent: Jan. 3, 2017

(54) METHOD FOR MEASURING THE THERMAL STABILITY OF A SUCCINIC ACID CRYSTAL INTENDED FOR THE PRODUCTION OF POLYMERS

(71) Applicants: Guillaume Fiey, Lille (FR); Marilyne Guillemant, Aire sur la Lys (FR); Jean-Michel Roturier, Armentieres (FR); Nicolas Jacquel, Lambersart (FR)

(72) Inventors: Guillaume Fiey, Lille (FR); Marilyne Guillemant, Aire sur la Lys (FR); Jean-Michel Roturier, Armentieres (FR); Nicolas Jacquel, Lambersart (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 14/381,326

(22) PCT Filed: Mar. 1, 2013

(86) PCT No.: PCT/FR2013/050438
§ 371 (c)(1),
(2) Date: Aug. 27, 2014

(87) PCT Pub. No.: WO2013/144471
PCT Pub. Date: Oct. 3, 2013

(65) Prior Publication Data
US 2015/0005469 A1 Jan. 1, 2015

(30) Foreign Application Priority Data
Mar. 2, 2012 (FR) .................................. 12 51924

(51) Int. Cl.
| | | |
|---|---|---|
| *G01N 21/25* | (2006.01) | |
| *C08G 63/16* | (2006.01) | |
| *G01N 21/84* | (2006.01) | |
| *C07C 51/50* | (2006.01) | |
| *C08G 63/78* | (2006.01) | |
| *G01N 21/29* | (2006.01) | |
| *G01N 21/94* | (2006.01) | |

(52) U.S. Cl.
CPC .............. *C08G 63/16* (2013.01); *C07C 51/50* (2013.01); *C08G 63/78* (2013.01); *G01N 21/25* (2013.01); *G01N 21/293* (2013.01); *G01N 21/84* (2013.01); *G01N 21/94* (2013.01); *Y10T 436/201666* (2015.01)

(58) Field of Classification Search
CPC ......... C08G 63/16; C08G 63/78; C07C 51/50; G01N 21/25; G01N 21/293; G01N 21/84; G01N 21/94; Y10T 436/201666; B07B 1/00; B07B 13/04
See application file for complete search history.

(56) References Cited

U.S. PATENT DOCUMENTS

| | | | |
|---|---|---|---|
| 5,132,456 | A | 7/1992 | King et al. |
| 5,143,834 | A | 9/1992 | Glassner et al. |
| 5,168,055 | A | 12/1992 | Datta et al. |
| 7,223,567 | B2 | 5/2007 | Ka-Yiu et al. |
| 7,985,566 | B2 | 7/2011 | Aoshima et al. |
| 8,021,864 | B2 | 9/2011 | Aoshima et al. |
| 2005/0042736 | A1 | 2/2005 | San et al. |
| 2006/0276674 | A1 | 12/2006 | Kushiku et al. |
| 2009/0171037 | A1 | 7/2009 | Aoshima et al. |
| 2011/0009531 | A1 | 1/2011 | Aoshima et al. |
| 2011/0288207 | A1 | 11/2011 | Aoshima et al. |
| 2013/0030145 | A1 | 1/2013 | Aoshima et al. |

FOREIGN PATENT DOCUMENTS

| | | |
|---|---|---|
| EP | 405 707 | 1/1991 |
| EP | 1 669 459 | 6/2006 |
| EP | 1 882 712 | 1/2008 |
| JP | 62-238232 | 2/1990 |
| WO | 2009/011974 | 1/2009 |
| WO | 2009/065778 | 5/2009 |
| WO | 2009/065779 | 5/2009 |
| WO | 2009/065780 | 5/2009 |
| WO | 2010/085731 | 7/2010 |
| WO | 2010/118932 | 10/2010 |
| WO | 2011/064151 | 6/2011 |

OTHER PUBLICATIONS

Feng, Lili, and Kris A. Berglund. "ATR-FTIR for determining optimal cooling curves for batch crystallization of succinic acid." Crystal growth & design 2.5 (2002): 449-452.*
International Search Report dated Jun. 25, 2013, corresponding to PCT/FR2013/050438.
"Testing Methods for Optical Properties of Plastics: JIS K 7105/ Testing Methods for Optical Properties of Plastics"; Japanese Industrial Standard, Tokyo, Japan, vol. JIS K 7105, Jan. 1, 1981.
Ailen M. Sanchez, et al.; "Novel Pathway Engineering Design of the Anaerobic Central Metabolic Pathway in *Escherichia coli* to Increase Succinate Yield and Productivity"; Mar. 7, 2005; pp. 229-239.

* cited by examiner

*Primary Examiner* — Lyle Alexander
*Assistant Examiner* — Robert Eom
(74) *Attorney, Agent, or Firm* — Young & Thompson

(57) ABSTRACT

A method for measuring the thermal stability of succinic acid includes the following steps: 1) preparing a succinic acid crystal powder having less than 1% residual water content; 2) placing 10 g of the crystal powder in an oven at 220° C. for 2 hours; 3) pulverizing and sieving the crystal powder processed in this way, such that the particle size distribution thereof is between 0 and 10%, and preferably between 4 and 6% for particles larger than 500 μm in size, between 20 and 40%, and preferably between 25 and 35% for particles between 200 and 500 μm in size, between 50 and 75% and preferably between 55 and 70% for particles smaller than 200 μm in size; and 4) measuring the color, in a spectrocolorimeter, of the pulverized and sieved powder and determining the average value of the yellow (index "b").

4 Claims, No Drawings

METHOD FOR MEASURING THE THERMAL STABILITY OF A SUCCINIC ACID CRYSTAL INTENDED FOR THE PRODUCTION OF POLYMERS

The present invention relates to a colorimetric method for qualifying crystalline succinic acid that is intended for the production of polymers, in particular of poly(butylene succinate) (or PBS) type.

When it is used as a starting material for the production of polymers, succinic acid must be of high purity in order to maintain the degree of polymerization and especially to prevent the colouration phenomena that can occur at the high temperatures used for the polymerization reaction.

The present invention thus provides a colorimetric test for determining the heat stability of the succinic acid used for producing polymers.

To this end, the present invention makes it possible to establish a correlation between the heat stability of crystalline succinic acid and the colour of the polymer produced.

Finally, this colorimetric method can be taken advantage of in order to identify the impurities involved in the colouration phenomena.

Succinic acid (or butanedioic acid) is an organic acid with two carboxyl groups, of semi-structural formula COOH—$CH_2$—$CH_2$—COOH, which is involved in cell metabolism, as a metabolic intermediate of the Krebs cycle in the mitochondrion.

However, it especially finds many applications in the cosmetics, food-processing, pharmaceutical and textile fields and in plastics. Thus, it is, for example, used as an intermediate for the synthesis of plastics, for the production of 1,4 butanediol, of tetrahydrofuran and of gamma-butyrolactone.

Moreover, succinic acid esters have the potential to be new "green" solvents which can replace the solvents most harmful to humans and to the environment.

Until recently, succinic acid was essentially produced via processes based on petrochemistry, but considered to be prejudicial to the environment. Alternatives to these processes have therefore been developed.

The production of succinic acid is thus currently carried out using renewable raw materials (in the case in point, by means of fermentation processes).

As a result, even though the origin of the succinic acid is of little importance here, the method for qualifying crystalline succinic acid according to the invention has especially been developed for characterizing biobased succinic acid.

Various bacteria are in fact known for their ability to produce succinic acid by fermentation, such as *Actinobacillus succinogenes*, *Mannheimia succiniciproducens* and *Escherichia coli*, just as are fungi such as *Aspergillus niger* and *Saccharomyces cerevisiae*.

Various fermentative processes are also described for efficiently producing succinic acid and for recovering/purifying succinic acid from the fermentation medium.

In this respect, those skilled in the art are constantly searching for new improved processes for purifying succinic acid produced by fermentation.

Indeed, fermentation products generally contain substantial amounts of impurities (biomass debris, sugars, amino acids, trace elements, salts, etc.) which are all colouration precursors capable, by their presence, even in trace amounts in the final product, of having an influence on the quality of the purified succinic acid and, consequently, on the quality of the polymer synthesized from said purified succinic acid.

A certain number of processes for removing said colouration precursors have therefore been proposed:

for removing nitrogenous impurities, U.S. Pat. No. 5,143,834 proposes a purification process which consists in subjecting in particular the fermentation medium containing the succinate to conventional electrodialysis, said electrodialysis also making it possible to concentrate the succinate in the aqueous phase;

for removing ionized substances, U.S. Pat. No. 5,132,456 describes bringing a liquid raw material containing a succinic acid salt into contact with an anion exchange resin so as to allow the resin to adsorb the succinic acid, and thus to free it of its anions.

The succinic acid is then eluted with an organic solvent (aqueous ammonia or the like);

JP 62 238 232 describes a method comprising a cation exchange resin for adsorbing the counterion of succinic acid and collecting the succinic acid as such;

with regard to EP 1 669 459, described therein is the use of a strongly acid cation exchange resin of H+ type for removing impurities of sodium ion, potassium ion, magnesium ion and ammonium ion type.

Likewise, this resin makes it possible to remove amino acids such as serine, glutamic acid, alanine, valine, methionine and tyrosine, which are difficult to remove by simple crystallization.

The concentration of cations other than H+ in the effluent is then ≤1.0%, preferably ≤0.5%;

in patent EP 0 405 707, the level of purity of the succinic acid prepared for commercial applications is indicated via its content of nitrogenous impurities (<1%) and of sulphates or other contaminating ions (<5 to 10 ppm);

patent EP 1 882 712 claims, moreover, the following:

a nitrogen atom content of 0.01 ppm or above, but of at most 2 000 ppm relative to the total amount of raw materials, a sulphur atom content of 0.01 ppm or above, but of at most 100 ppm relative to the total amount of raw materials.

It thus appears that there are as many thresholds to be observed with respect to certain colouration precursor impurities as there are methods of purification designed to remove them.

However, the conventional methods for quantifying colouration precursor impurities are not precise enough to allow categorization of succinic acid samples with regard to their respective quality for the production of polymers.

As a result, to the knowledge of the applicant company, no reliable colorimetric method for distinguishing the batches of succinic acid produced is described in the literature.

From the aforementioned, it follows that there remains an unsatisfied need to have available an effective, rapid and simple method for qualifying crystalline succinic acid intended for the production of polymers, in particular of poly(butylene succinate) (or PBS) type.

The applicant company has thus found that this need can be satisfied by the development of a rapid colorimetric method for determining the heat stability of the succinic acid produced, which, moreover, manages to dispense with knowledge of the nature of the precursor impurities involved.

This method therefore consists in measuring the colouration generated after heat treatment of crystallized succinic acid.

This colorimetric measurement of the crystalline succinic acid is carried out on a spectrocolorimeter (for example the Dataflash 100 instrument sold by the company Datacolor), by determining the mean white balance (L), red balance (a) and yellow balance (b) of a crystallized succinic acid sample.

As will be presented hereinafter, the heat stability of the succinic acid will be more particularly expressed by its yellow balance value (termed "index b").

The method for measuring the heat stability of succinic acid therefore comprises the following steps:

1) preparing a crystalline powder of succinic acid having a residual water content of less than 1%,
2) placing a sample of said crystalline powder in an oven at 220° C. for 2 h,
3) milling and sieving the crystalline powder thus treated, in such a way that its particle size distribution is:
   between 0 and 10%, preferably between 4 and 6%, for the particles with a size greater than 500 μm,
   between 20 and 40%, preferably between 25 and 35%, for the particles with a size between 200 and 500 μm,
   between 50 and 75%, preferably between 55 and 70%, for the particles with a size less than 200 μm,
4) measuring the colour of the milled and sieved powder in a spectrocolorimeter and determining the mean yellow value (index "b").

The first step of the method in accordance with the invention consists in preparing a crystalline powder of succinic acid having a residual water content of less than 1%.

The production of the succinic acid per se can be carried out by any means known, moreover, to those skilled in the art: chemically, but especially by fermentation.

Advantageously, the succinic acid can be prepared from recombinant yeasts, as taught in patent applications WO 2009/011974, WO 2009/065780, WO 2009/065779, WO 2010/085731 or WO 2010/118932.

The succinic acid can be extracted from the fermentation medium by various methods, such as, for example, that described by the applicant company in its international patent application WO 2011/064151.

The method thus makes it possible to obtain succinic acid crystals of high purity (>99.5%/dry basis)—with an overall recovery yield>90%.

The second step of the process in accordance with the invention consists in placing a sample of said crystalline powder in an oven at 220° C. for 2 h.

The process consists more particularly in preparing a sample of exactly 10 g of crystalline succinic acid, of placing it in a tube resistant to high temperature, and in placing it at 220° C. in a ventilated oven for 2 h.

The third step of the process in accordance with the invention consists in milling and sieving the crystalline powder thus treated, in such a way that its particle size distribution is:

between 0 and 10%, preferably between 4 and 6%, for the particles with a size greater than 500 μm,
between 20 and 40%, preferably between 25 and 35%, for the particles with a size between 200 and 500 μm,
between 50 and 75%, preferably between 55 and 70%, for the particles with a size less than 200 μm.

It is recommended to leave the tube containing the succinic acid thus heat treated to stand for a minimum of three hours before producing the pellet that will be read on the colorimeter.

The production of said pellet cannot be carried out on the powder as such, given the phenomena of caking subsequent to the heat treatment.

It is therefore necessary to carry out fine milling of the agglomerates thus obtained.

The milling is thus carried out by any means known to those skilled in the art, i.e. manually, in a mortar, or mechanically, so as to obtain the particle size distribution of the powder as presented.

This particle size distribution is determined by dry-phase sieving on a vibrating sieve conventionally accessible to those skilled in the art, according to the recommendations for use advocated by the manufacturer of the vibrating sieve selected.

This forming facilitates the production of the pellet, according to the specifications of the spectrocolorimeter manufacturer.

The fourth step of the process in accordance with the invention consists in measuring the colour in a spectrocolorimeter and in determining the mean yellow value (index "b").

The colorimetric measurement is based on the opposite colours theory which specifies that the responses of the cones (cells of the retina of the human eye that are responsible for colour vision) to the colours red, green and blue are recombined into opposite signals "black-white", "red-green" and "yellow-blue" when transmitted to the brain by the optic nerve.

This measurement is based on the colour scales widely used in the food industries and polymer industries, called Hunter L, a, b scales.

They are three-dimensional scales.

The scales of L, a and b type are defined in the following way:

"L" axis (luminosity): 0 corresponds to black, 100 corresponds to white;
"a" axis (red-green): the positive values are attributed to red; the negative values are attributed to green; 0 is neutrality;
"b" axis (yellow-blue): the positive values are attributed to yellow; the negative values are attributed to blue; 0 is neutrality.

The index "L" therefore has a value between 0 and 100, while the indices "b" and "a" do not have numerical limitations.

The measuring device is conventionally a spectrocolorimeter (allowing measurement of reflection at wavelengths of between 400 and 700 nm), such as the Dataflash 100 sold by the company Datacolor (measurement aperture: "9 mm in diameter"; reading illuminant: "C2 Deg").

For the crystalline succinic acid, the measurement of the index "b" makes it possible by itself to qualify for its polymer application, as will be demonstrated hereinafter.

The colorimetric method according to the invention makes it possible to categorize the crystalline succinic acid produced.

Thus, a subject of the present invention is a method for preparing a succinic acid polymer, preferably poly(butylene succinate) (or PBS), using, as raw material, a succinic acid selected by means of the method for measuring heat stability described above. This method for preparing a succinic acid polymer is in particular characterized in that the succinic acid has a mean yellow value of less than or equal to 2.

In order to demonstrate this, the applicant company undertook two series of experiments having the objective of testing the impact of the colouration of the monomer on the level of colouration of polymers produced from various batches of succinic acid, of chemical and especially fermentative origin, the chemical quality being considered here a positive control:

determination of the index "b" for various batches of succinic acid produced fermentatively from strains of recombinant microorganisms of *E. coli* or *S. cerevisiae* type, and measurement of the colouration of the corresponding polymer.

This first experiment thus made it possible to define a threshold value for the index "b" of 1.9, below which the crystalline succinic acid can be retained for the PBS polymer application in particular;

qualitative and quantitative determination of the impurities capable of acting as precursors for colouration of the succinic acid produced fermentatively.

As regards the colouration of the polymer produced from the succinic acid (in the case in point, PBS), it is conventionally determined on a spectrophotometer (for example, DYK Gardner TCS II—observation angle of 10°, illumination D65), by also determining the mean white balance (L), red balance (a) and yellow balance (b).

The colouration of the polymer will then be expressed by its yellow balance value (referred to here as "Yellow index").

EXAMPLE 1

Fermentative Production, Extraction and Purification of Succinic Acid

A first series of fermentations with a recombinant *E. coli* (in this case the strain SBS550MG-pHL413 described in Sanchez et al., *Metabolic Engineering*, 7 (2005) 229-239, and in documents U.S. Pat. No. 7,223,567 and US 2005/0042736) is carried out.

A second series of fermentations is also carried out, with a recombinant strain of *S. cerevisiae* (in this case that described in patent application WO 2009/065778).

The extraction of the succinates and the purification of the succinic acid are carried out from these fermentation media by the succession of the following steps:

Removal of Insoluble Organic Impurities (Biomass and Cell Debris)

The removal is carried out by tangential filtration with tangential flow on a membrane having a pore diameter of 100 nm, at between 40 and 80° C. (ceramic membrane with a channel diameter of 3.5 mm).

The temperature is maintained preferentially at 60° C. with a transmembrane pressure of 1 bar and with diafiltration with 20% of demineralized water.

Under these conditions, the flow is approximately 90 L/h/m$^2$ and the permeate obtained is clear and bright. The permeate still contains more than 6000 ppm of soluble organic impurities, in this case soluble organic nitrogen.

Removal of Soluble Organic Impurities (Residual Soluble Proteins)

This removal consists in adsorbing the organic nitrogen on activated carbon or in denaturing it before removing it by filtration. In the case of denaturing, the procedure may be thermal or osmotic.

A contact zone at 80° C. is used which allows the proteins to be flocculated for 10-15 min. The solution is then filtered through a filter with a pore diameter of 0.22 μm.

This step of removing organic nitrogen becomes optional when the microfiltration is carried out at 80° C. This is because, in that case, there is simultaneous denaturing of the organic nitrogen and retention on the microfiltration membrane.

Chelation and Acidification

The maximum admissible concentration for feeding to bipolar electrodialysis (BED) in terms of divalent cations ($Ca^{2+}$, $Mg^{2+}$, etc.) is 5 ppm. This is because the divalent cations present will react with the hydroxyl ions on the water electrolysis membranes to form salts of very low solubility, which crystallize in the membranes and make them permeable.

In order to protect the integrity of the BED membranes, a chelation step is carried out in order to reach the safety threshold of 5 ppm.

This step consists in complexing the divalent cations using aminophosphonic functions (Purolite S940, Amberlite IRC747, etc.) or diacetic functions (Purolite S930, Lewatit TP208) grafted onto cation exchange resin.

In order to do this, the solution is supplied at 60° C., at a flow rate of 2 BV/h. Under these conditions, the volume of solution treated may reach 30 to 40 times the resin bed volume.

Once it has been freed of these divalent cations, the solution can be acidified by BED. The module used is a stack from the company Eurodia: EUR6.

This stack consists of two types of membranes:
bipolar membranes, which allow the electrolysis of water ($H_2O \rightarrow H^+ + OH^-$) and the acidification of the succinates,
cationic membranes, which allow the selective transfer of the monovalent cations.

The electrolysis and the transfer of the cations are carried out by virtue of a potential difference which is applied to the system by a generator.

The succinate salt is then acidified over time by the $H^+$ ions released by the electrolysis of the water. In the same way, the monovalent cations are alkalinized by the hydroxyl ions after migration through the cationic membranes, to give a base again which can be recycled to the fermentation.

The flow of cations transferred is approximately 22 eq/h/m$^2$ for a conversion rate of 90%, which equates to a final pH of approximately 3.5.

The acidification is finished on strong cationic resin (Purolite C150). This is because the last equivalents are very difficult to transfer, and hence the energy consumption of the operation is greatly increased (limitation mainly due to the osmotic pressure).

The treatment is preferentially carried out at 40° C. and at 2 BV/h. The volume of solution treated is then approximately 10-15 BV.

The pH of the solution after treatment on cationic resin is equal to 2 and contains succinic acid in its low-solubility form (free acid).

Crystallization

The acidified solution is concentrated by evaporation of water on a Wiegand® falling-film evaporator. The concentration factor is about 5 to 10 depending on the initial concentration of succinic acid.

The factor here is equal to 8, in order to obtain supersaturation.

The concentration of the solution is then 420 g/L at 80° C., which corresponds to the supersaturation of the solution.

The solution is then cooled by direct contact from 80 to 20° C. at a rate of 5° C./h.

Crystallization begins spontaneously from the beginning of cooling, but seeding may be carried out in order to better control the physical properties of the crystallized succinic acid.

After separation on a Rousselet® centrifuge and washing with one volume of demineralized water per cake volume, the crystals are dried.

At this step, the crystallization yield is >85% for a succinic acid purity of 99.7%/dry basis.

Redissolution

The redissolution of the crystals is carried out in demineralized water at 60° C. rather than at 20° C., in order to reduce the consumption of demineralized water.

For the same purpose, the mother liquor and/or the water from washing the highly pure crystals can also be recycled at this step. The overall yield of succinic acid is then also optimized.

Finishing Treatment

This step consists of a decolorizing treatment and a demineralization step. The decolorizing can be carried out with activated carbon or by ozonation.

Treatment with activated carbon has the major advantage of fixing the orotic acid, a nitrogenous impurity which has a very low solubility and which crystallizes with the succinic acid.

In batch mode, the amount of Norit SX$^+$ activated carbon is 1% in relation to the succinic acid. After 1 h of reaction at 60° C., the solution is filtered on a 3 μm candle filter.

The solution is then treated for demineralization at 2 BV/h at 60° C.

Carried out successively on Purolite® C150 strong cationic resin and then Daion® WA30 weak anionic resin, the treatment allows removal of the traces of inorganic cations and anions, on the one hand, and of fumaric acid, on the other hand. Furthermore, the weak anionic resin allows additional decolorizing.

Following treatment on weak anionic resin, the fumaric acid content may be reduced by a factor of 20 and the residual colouring is zero.

Crystallization

The solution which has purified can then be crystallized under the same conditions as the previous step.

The yield of this crystallization step is also >85%. The mother liquor and the washing water are recycled to the dissolution of the technical-grade crystals. The overall yield of this step may thus approach 100%. The purity of the crystals is more than 99.8%.

EXAMPLE 2

Colorimetric Measurement of the Succinic Acid Produced by Fermentation of Recombinant Microorganisms Three successive fermentations were carried out for the *E. coli* strain (tests "A" to "C"); 6 for the *S. cerevisiae* strain (tests "D" to "I") and the succinic acid was extracted and purified under the conditions of example 1.

The nine samples of crystalline powder of succinic acid are then analyzed according to the method in accordance with the invention.

10 g of each of these samples were placed in an oven at 220° C. for 2 h 15. The powder recovered was milled and analysed in a spectrocolorimeter in accordance with the method of the invention.

Table 1 below gives the values of the indices "L", "a" and "b" as obtained.

TABLE 1

| | Samples | | |
|---|---|---|---|
| | "L" | "a" | "b" |
| "Chemical" succinic acid | 98.0 | 0.00 | 1.3 |
| "A" | 91.1 | 0.99 | 6.2 |
| "B" | 97.3 | 0.19 | 1.8 |
| "C" | 97.1 | 0.14 | 1.9 |

TABLE 1-continued

| | Samples | | |
|---|---|---|---|
| | "L" | "a" | "b" |
| "D" | 96.9 | 0.00 | 2.1 |
| "E" | 96.5 | 0.29 | 2.3 |
| "F" | 97.4 | 0.16 | 1.7 |
| "G" | 97.3 | 0.14 | 1.7 |
| "H" | 98.1 | 0.11 | 1.1 |
| "I" | 97.3 | 0.23 | 1.9 |

Compared with the reference chemical succinic acid sample (sold by the company Sigma), it appears here that only sample "H" would have the required colorimetric quality.

In order to demonstrate this, polymerization tests with these various qualities were undertaken.

Samples of PBS are synthesized via a two-step polycondensation reaction, in a 7.5 l stainless steel reactor equipped with a heating system, a mechanical stirrer, a distillation column, a vacuum line and a nitrogen gas inlet.

1889 g (16 mol of succinic acid) and 1513.7 g (16.8 mol) of 1,4 butanediol (BDO) are charged to the reactor.

The reaction mixture is then heated at 225° C. at 2 bar of nitrogen pressure and stirred at a constant speed of 150 rpm.

A mixture of water and tetrahydrofuran (1 to 2.5 mol % of THF) produced from the esterification and from the cyclization of the BDO are removed from the reactor by the distillation column.

The degree of esterification is estimated via the amount of distillate collected.

In a second step, the pressure is reduced to 0.7 mbar over the course of 120 minutes.

The reaction is catalyzed by 3.914 g of Ti(OBu)$_4$ (Ti=200 ppm), which are added to the reactor during the step of decompression (approximately 20 mbar) in order to prevent as much as possible any contact with the residual water.

The pressure conditions are maintained for 3.8 hours.

The polymer is removed from the reactor and immersed in water. Approximately 15 mg of PBS granules are obtained after granulation.

The degree of colouring of the polymer is then determined on polymerized sheets having the same thickness (of about 3 mm) using a Dyk Gardner TCS II spectrophotometer (observation angle of 10°, illuminant D65).

The results are also expressed by the indices "L", "a" and "b", and more particularly by the measurement of the yellow index (abbreviation: YI).

The YI is in fact calculated using the following equation (ASTM D1925):

$$YI = \frac{100 \times (1.28 X_{CIE} - 1.06 Z_{CIE})}{Y_{CIE}}$$

Table 2 below gives the YI of the polymers produced from two different samples of biobased succinic acid of known index "b", on either side of the threshold for the value of the index "b" established hereinabove, i.e. index "b"=2.

TABLE 2

| PBS prepared from: | Index "b" | YI |
|---|---|---|
| 2 batches of succinic acid produced chemically | 1.3 | 7.8 |
| | 1.3 | 6.1 |
| "H" | 1.1 | 6.5 |

TABLE 2-continued

| PBS prepared from: | Index "b" | YI |
|---|---|---|
| "F" | 1.7 | 9.8 |
| "D" | 2.1 | 11 |

A PBS is considered to be correct by those skilled in the art if its YI is <10.

These results make it possible to confirm the good quality of the succinic acid "H", and to show that it is possible to go up to an index "b" value of 1.7 for producing an acceptable BPS colorimetric quality.

EXAMPLE 3

Confirmation of the Threshold Value of the Index "b" of the Biobased Succinic Acid: Enrichment of a Reference Succinic Acid with Various Impurities of Defined Nature and Amount The impurities capable of acting as colouration precursors conventionally identified in fermentation media are in particular residual substances such as carbohydrates, inorganic or organic nitrogen, inorganic sulphur and some organic acids coproduced by these strains.

In order to test the robustness of the crystalline succinic acid qualification method of the invention, and the predicted use that could be made of said method, a succinic acid of chemical origin (reference index "b"=1.3) or biobased origin (succinic acid corresponding to batch "H" of example 1—reference index "b"=1.1) is artificially enriched with impurities representative of what is found in said fermentation media before carrying out the treatment in an oven at 200° C.

The contaminants selected are the following (tested at the amounts indicated):
- carbohydrate: glucose at concentrations of about 100 ppm;
- organic nitrogen: valine at a concentration of 200 ppm for succinic acid of chemical origin; 1000 ppm for the biobased succinic acid;
- sulphur: $Na_2SO_4$ at the concentration of 200 ppm for the succinic acid of chemical origin; 1000 ppm for the biobased succinic acid;
- organic acids: fumaric acid, malic acid at the concentration of 1000 ppm, tested only with the succinic acid of chemical origin;
- sulphur-comprising organic acid: orotic acid at the concentration of 1000 ppm, tested only with the succinic acid of chemical origin;
- sulphur and nitrogen: ammonium sulphate at 1200 ppm, tested only with the biobased succinic acid.

The results obtained are given in Table 3 below.

TABLE 3

| Samples | Index "b" | Δ (b − b.ref) |
|---|---|---|
| Chemical SA + 100 ppm of glucose | 3.3 | 2 |
| Tests "H" + 100 ppm of glucose | 3.2 | 2.1 |
| Chemical SA + 200 ppm of valine | 1.5 | 0.2 |
| Tests "H" + 1000 ppm of valine | 1.3 | 0.2 |
| Chemical SA + 100 ppm of glucose + 200 ppm of valine | >5 | >4 |
| Chemical SA + 200 ppm of $Na_2SO_4$ | 1.3 | 0 |
| Tests "H" + 1000 ppm $Na_2SO_4$ | 1.2 | 0.1 |
| Chemical SA + 1000 ppm of fumaric acid | 1.7 | 0.5 |
| Chemical SA + 1000 ppm of malic acid | 1.5 | 0.2 |
| Chemical SA + 1000 ppm of orotic acid | 2 | 0.7 |
| Tests "H" + 1200 ppm of ammonium sulphate | 2 | 0.9 |

These results demonstrate:
- The importance of residual glucose alone in the heat stability of the biobased succinic acid;
- the nitrogenous contaminants cause only a slight modification of the heat stability of the succinic acid;
- the combination of the nitrogenous and sulphur-comprising contaminants amplifies the colouration phenomenon.

In this respect, the applicant company goes against a technical prejudice which claims that only the nitrogenous and sulphur-comprising impurities must be controlled (cf. patent EP 1 882 712 mentioned hereinabove);
- the succinic acid derivatives (malic acid and fumaric acid) and also the sulphur ($Na_2SO_4$) have no more significant impact than the colouration of the chemical succinic acid taken as reference,
- the nitrogenous contaminants cause only a slight modification of the heat stability of the succinic acid.

In order to complete this work, PBS was produced from various batches of chemical succinic acid enriched in impurities (those above and other samples prepared specially for this second series of tests).

Table 4 below gives the results of YI measured for each of the polymers produced.

TABLE 4

| PBS produced with | N (ppm) | S (ppm) | index "b" of the monomer | "Yellow index" of the PBS |
|---|---|---|---|---|
| a first reference chemical succinic acid | 0 | 0 | 1.3 | 7.8 |
| a second reference chemical succinic acid | 0 | 0 | 1.3 | 6.1 |
| +1000 ppm of fumaric acid | 0 | 0 | 1.7 | 9.8 |
| +1000 ppm of malic acid | 0 | 0 | 1.5 | 4.6 |
| +1000 ppm of orotic acid | 179 | 0 | 2 | 15.7 |
| +200 ppm of $Na_2SO_4$ | 0 | 45 | 1.3 | 2.8 |
| +200 ppm of valine | 24 | 0 | 1.5 | 3.9 |
| +20 ppm of glucose | 0 | 0 | 2.5 | 11.3 |
| +100 ppm of glucose | 0 | 0 | 3.3 | 18.1 |
| +100 ppm of glucose + 200 ppm of valine | 24 | 0 | 4 | 15.5 |

These first results confirm the influence of the glucose and orotic acid impurities on the quality of the polymer, as on that of the monomer.

Moreover, if the curve plotting the values of the index "b" of the monomer as a function of the YI of the polymer is produced, and a PBS of correct colouration when its YI is ≤10 is always taken as reference, a threshold value for the index "b" of about 2 is found.

The invention claimed is:
1. A method for measuring the heat stability of succinic acid, the method comprising the following steps:
 1) preparing a crystalline powder of succinic acid having a residual water content of less than 1%,

2) placing a sample of said crystalline powder in an oven at 220° C. for 2 h, 3) milling and sieving the crystalline powder thus treated, in such a way that its particle size distribution is:

between 0 and 10%, for particles with a size greater than 500 μm, between 20 and 40%, for particles with a size between 200 and 500 μm, between 50 and 75%, for particles with a size less than 200 μm, 4) measuring the colour of the milled and sieved crystalline powder in a spectrocolorimeter and determining a mean yellow value (index "b").

2. A method for preparing a succinic acid polymer, comprising the following steps:

(1) preparing a crystalline powder of succinic acid having a residual water content of less than 1%;

(2) placing a sample of said crystalline powder in an oven at 220° C. for 2 h;

(3) milling and sieving the crystalline powder thus treated, in such a way that its particle size distribution is:

between 0 and 10% for particles with a size greater than 500 μm, between 20 and 40% for particles with a size between 200 and 500 μm, and between 50 and 75% for particles with a size less than 200 μm;

(4) measuring the color of the milled and sieved crystalline powder in a spectrocolorimeter and determining a mean yellow value (index "b");

(5) selecting a succinic acid having a mean yellow value of less than or equal to 2 as a raw material for the succinic acid polymer, and preparing the polymer with the selected succinic acid.

3. The method of claim 2, comprising:

(3) milling and sieving the crystalline powder thus treated, in such a way that its particle size distribution is between 4 and 6% for particles with a size greater than 500 μm, between 25 and 35% for particles with a size between 200 and 500 μm, and between 55 and 70% for particles with a size less than 200 μm.

4. The method of claim 2, wherein the succinic acid polymer is poly(butylene succinate).

\* \* \* \* \*